(12) United States Patent  
Berlin et al.

(10) Patent No.: US 8,271,242 B2
(45) Date of Patent: Sep. 18, 2012

(54) METHOD AND APPARATUS FOR MODELLING AND SIMULATING OPTICAL PROPERTIES OF SPECIAL EFFECT PAINTS AND FOR DETERMINING ILLUMINATION AND MEASUREMENT GEOMETRIES FOR SPECTRAL PHOTOMETERS

(75) Inventors: Harald Berlin, Nottuln (DE); Clemens Baumeister, Muenster (DE); Christian Bornemann, Muenster (DE); Josef Kallrath, Weisenheim am Berg (DE)

(73) Assignee: BASF SE, Ludwigshafen (DE)

( * ) Notice: Subject to any disclaimer, the term of this patent is extended or adjusted under 35 U.S.C. 154(b) by 357 days.

(21) Appl. No.: 12/528,808

(22) PCT Filed: Oct. 21, 2008

(86) PCT No.: PCT/EP2008/008890
§ 371 (c)(1),
(2), (4) Date: Aug. 27, 2009

(87) PCT Pub. No.: WO2009/071152
PCT Pub. Date: Jun. 11, 2009

(65) Prior Publication Data
US 2010/0049484 A1    Feb. 25, 2010

(30) Foreign Application Priority Data

Dec. 7, 2007  (EP) ................................... 07023733

(51) Int. Cl.
*G06F 7/48* (2006.01)

(52) U.S. Cl. .......................................................... 703/6
(58) Field of Classification Search ........................ 703/6
See application file for complete search history.

(56) References Cited

U.S. PATENT DOCUMENTS

| 6,064,487 A | 5/2000 | Kettler et al. |
| 6,745,158 B1 * | 6/2004 | Eickmeyer et al. ............... 703/2 |
| 7,045,169 B2 * | 5/2006 | Freeman et al. ............... 427/180 |

FOREIGN PATENT DOCUMENTS

| DE | 196 52 885 | 6/1998 |
| DE | 197 20 887 | 11/1998 |

* cited by examiner

*Primary Examiner* — Eunhee Kim
(74) *Attorney, Agent, or Firm* — Oblon, Spivak, McClelland, Maier & Neustadt, L.L.P.

(57) ABSTRACT

A method that is suitable for modelling and simulating optical properties in special effect paints which contain pigments with isotropic light-scattering properties and pigments with anisotropic light-scattering properties, and the effect-producing substances form at least one layer of material or coat of paint on a suitable substrate. The method is characterised in that the isotropically light-scattering pigments and the anisotropically light-scattering pigments are virtually separated such that the isotropically light-scattering pigments virtually form the layer of material and the anisotropically light-scattering pigments are virtually arranged on the edge surfaces of the layer of material. The optical properties of the virtual layer of material of the isotropically light-scattering pigments are determined by linear differential equations and the optical properties of the anisotropically light-scattering pigments are taken into consideration as boundary conditions, by means of specific effect operators.

12 Claims, 7 Drawing Sheets

Figure 1 anisotropically light-scattering pigments 202 isotropically light scattering pigments 201

Figure 7 layer thickness

Figure 8 layer thickness

METHOD AND APPARATUS FOR MODELLING AND SIMULATING OPTICAL PROPERTIES OF SPECIAL EFFECT PAINTS AND FOR DETERMINING ILLUMINATION AND MEASUREMENT GEOMETRIES FOR SPECTRAL PHOTOMETERS

TECHNICAL FIELD

The present specification relates to a method and an apparatus for modelling and simulating optical properties of special effect paints, particularly a method and an apparatus for modelling and simulating optical properties of special effect paints with isotropically and anisotropically light-scattering pigments and for reproducing a shade of colour or a formulation for a colour template for a special effect paint.

BACKGROUND

Various physical models are used to produce calculations of primary formulations and corrections for paints, e.g. according to Kubelka-Munk and Giovanelli, enabling the optical properties of the paints to be calculated and simulated. These optical properties are determined essentially by the nature of the pigments contained in the paint. A distinction can be drawn between isotropically and anisotropically light-scattering pigments. The isotropically light-scattering pigments cause multiple scattering of the incident light, so that the intensity of the reflected or scattered light is independent of both the direction of irradiation of the incident light and also the direction of observation. As a result of the multiple scattering the intensity of the reflected and scattered light is at least approximately isotropic. By contrast, the intensity of the reflected light in the case of anisotropically light-scattering pigments is dependent on the direction of irradiation of the incident light and on the direction of observation, as will be shown in more detail hereinafter.

A physical model used for calculating and simulating the optical properties of paints uses a so-called radiation transport equation (RTE) in which the light intensity depending on the directions of scattering of the light-scattering pigments of the paint is described in the form of a phase function. In the case of the isotropically light-scattering pigments as used in conventional paints, the phase function is a constant. Therefore, the radiation transport equation, which is dependent on the angle and layer thickness, can be described approximately by a linear differential equation system with constant coefficients and can be solved easily and efficiently in terms of computing time using an eigenvalue approach. The radiation transport equation is thus replaced by a linear differential equation system. However, the approximate simplification of these physical models can only be used for pigments with isotropically light-scattering properties.

In contrast to the conventional paints, so-called special effect paints additionally contain, besides the pigments with isotropically light-scattering properties, anisotropically light-scattering pigments which impart anisotropically light-scattering properties to the corresponding paints. These include aluminium and/or interference pigments such as for example mica particles or mica, which produce a so-called "pearlescent" effect in car paints, for example.

As the use of anisotropically light-scattering pigments results in a variable light intensity distribution of the reflected or scattered light when the corresponding coat of paint is irradiated, which is dependent not only on the direction of illumination and observation but also on an optical layer thickness, the phase function is not constant in this case, in contrast to the purely isotropically light-scattering pigments. For special effect paints an angle-dependent phase function thus has to be applied but then there is no longer an easily solvable linear differential equation system available. This can no longer be solved as a closed equation and therefore significantly greater numerical computing time has to be expended.

SUMMARY

The present specification therefore proposes a method of using a physical model of isotropically light-scattering pigments for a special effect paint with anisotropically light-scattering pigments, by means of which even for anisotropically light-scattering pigments, as an approximation, a linear differential equation system with constant coefficients can be provided for achieving a simple and time-efficient solution.

The method makes it possible to model and simulate optical properties in special effect paints which contain both pigments with isotropic light scattering properties and also pigments with anisotropic light scattering properties, the special effect paints forming at least one layer of material or coat of paint on a suitable substrate.

The method also makes it possible to reproduce a shade of a colour template for a special effect paint of this kind by determining the optical properties of this colour template with a colour test pattern of a formulation for a paint mock-up such as a colour test plate, for example, and comparing them by a comparison process. Using the comparison a correction to the formulation for the paint mock-up is calculated so that it is possible to match the shades of the two paints, both the paint of the colour template and the paint of the colour test pattern or paint mock-up.

According to the proposed method the isotropically light-scattering pigments and the anisotropically light-scattering pigments are virtually spatially separated such that the isotropically light-scattering pigments form virtually at least one layer of material and the anisotropically light-scattering pigments are virtually arranged on the edge surfaces of this layer of material, so that the optical properties of the virtual layer of material formed by the isotropically light-scattering pigments can be determined by linear differential equations. The optical properties of the anisotropically light-scattering pigments, on the other hand, are taken into consideration, by specific effect operators, as boundary conditions for solving the linear differential equation. A detailed representation of the effect operators is given in Appendix 2.

The layer of material may for example consist of a double layer, while the anisotropically light-scattering pigments are virtually arranged on an inner edge surface of the double layer. By the inner edge surface is meant the edge surface that is arranged between the two layers of the double layer.

This means that the "normal" isotropically light-scattering pigments are virtually spatially separated from the anisotropically light-scattering pigments according to the proposed method. Obviously, this separation need not be restricted to a virtual layer or double layer of material. Rather, the virtual layer of material of the isotropically light-scattering pigments may comprise, or be formed from, a virtual stacked multilayered structure having a plurality of virtual layers. For each of these virtual layers, the anisotropically light-scattering pigments are arranged on the respective edge surfaces of the virtual layers.

According to another embodiment, the anisotropically light-scattering pigments are arranged exclusively on the respective inner edge surfaces.

On average, the anisotropically light-scattering pigments incorporated in the paint layer of a special effect paint do not have any azimuthal dependency where the geometry of the illumination is perpendicular or annular, which means that the radiation transport equation can also be dealt with in azimuth-independent manner. It is therefore assumed that the normal isotropically light-scattering pigments are continuously distributed throughout the virtual layer or throughout all the virtual layers. The effect of the anisotropically light-scattering pigments is thus shifted, with the aid of specially developed effect operators, to the boundary conditions of the linear differential equation system. Thus, the effect-specific properties of the anisotropically light-scattering pigments are to be taken into consideration exclusively at the edge surfaces (optionally only on the inner edge surfaces) by means of the boundary conditions of the differential equation system. The effect operators themselves may be represented by suitable matrix multiplications, as shown in detail by way of example in Appendix 2.

As described hereinbefore, these boundary conditions act on the edge surfaces (optionally only on the inner edge surfaces) of the virtual layers. Within the virtual layers, the effect of the normal isotropically light-scattering pigments can thus be described by the constant phase function of the corresponding radiation transport equation, so that this method also retains simplicity and time efficiency in the calculation of the radiation transport equation. This permits effective angle-dependent calculation of the radiation transport equation for special effect paints with different layer thickness, and with an azimuth-independent direction of illumination.

The method also makes it possible to calculate illumination angles of spectrophotometric measuring equipment that fit the physical model of the simulation, taking into account refractive indices of the corresponding paint and discrete angles that are obtained from a quadrature formula, corresponding to the basic problem, for solving the radiation transport equation.

Figure 4A:
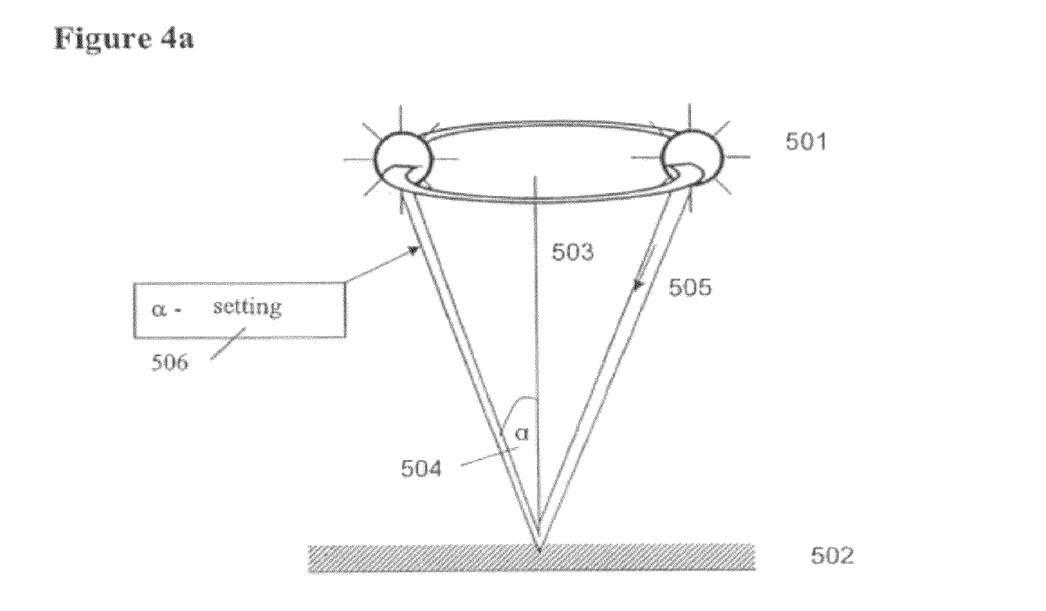
FIG. 4a shows a schematic representation of an apparatus for applying annular illumination.
Figure 4B:
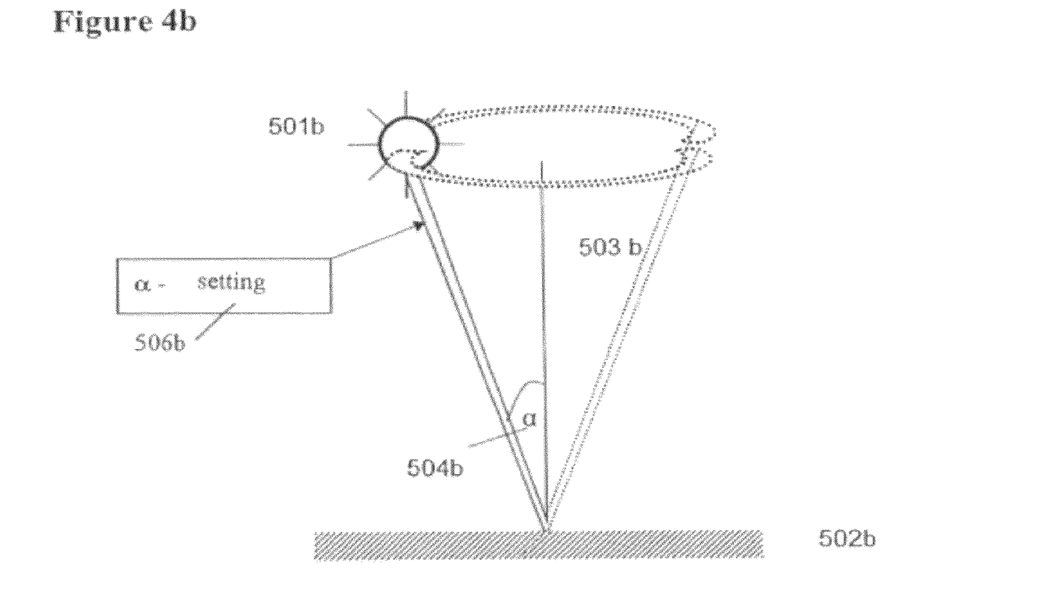
FIG. 4b shows a schematic representation of an apparatus for applying virtual annular illumination.

When calculating the illumination angle or angles, an optical phase transition e.g. from air to paint has to be taken into consideration. This leads, via the so-called "Fresnel" relation, to a change in the direction of an optical path of the incoming light during the transition into the layer of paint. A beam entry direction of the illumination should be selected so that the beam direction altered by the phase transition in the paint layer coincides with a direction that is prescribed by the quadrature formula. Reference is made here to FIGS. 4a and 4b which will be described hereinafter and to an apparatus 506 or 506b, which is provided for adjusting the beam entry direction.

Apart from the modelling and simulation of an individual layer of a special effect paint which is virtually separated into a multilayered structure, it is also possible for the method to be applied to an actual multilayered paint structure. This means that the virtual stacked multilayered structure corresponds to an actual multilayered structure of a special effect paint or is equated with such. For example, this actual multilayered paint structure may consist of an electrolytically deposited primer layer, a coat of filler paint, a base coat and a clear varnish applied on top. In this case, too, specific optical properties of the paint layers may be taken into account in the boundary conditions for solving the corresponding linear differential equations. The method described is thus also suitable for determining the influence of coloured substrates or a clear varnish on the actual shade of colour of a multilayered paint structure.

The anisotropically light-scattering pigments that are added to modern paints as effect-producing substances comprise, as described hereinbefore, for example metallic reflective particles (e.g. so-called "silver dollars") or flakes or particles of mica which have a refractive index of about n=3, for example. These anisotropically light-scattering pigments are pigments or particles measuring up to several μm in size, which are significantly larger than the normal isotropically light-scattering pigments measuring about 0.1 μm.

The virtually preferred arrangement of the anisotropically light-scattering pigments on the edge surfaces of the virtual layers as described above ensures that the anisotropically light-scattering pigments do not have to be dealt with in the differential equations but are taken into account by means of the boundary conditions. A surface density ($\eta$) of the anisotropically light-scattering pigments, their angular distribution ($\sigma$) and an optical layer thickness ($\tau$) of the paint layer have to be taken into consideration with respect to the isotropically scattering pigments. A detailed explanation regarding their consideration is provided in Appendix 2.

In the production of paints, as described hereinbefore, the physical models can be used to calculate the appropriate measures such as corrective formulations, for example, with which a production batch can be adjusted to a prescribed colour template or colour shade specification. This process is known as so-called "model-aided process control".

However, the production of special effect paints in particular requires a model such as the one described here which can take account of the angle-dependent influences of the anisotropically light-scattering pigments.

Moreover, during production, the optical properties of the special effect paints can be altered by means of additives that change the angular distribution of the anisotropically light-scattering pigments. In addition, the nature of the anisotropically light-scattering pigments that influence the angular distribution as well as the solvent balance can be changed, as the kinetics of the volatilisation of the solvent affect the angular distribution of the anisotropically light-scattering pigments. These changes to the optical properties can also be taken into account by a suitable adaptation of the boundary conditions or effect operators for the anisotropically light-scattering pigments by the method described.

Using the method described, by real measurements it is thus possible to reproduce a colour template by measuring and comparing the optical properties of the colour template and a colour test pattern of a formulation of a paint mock-up—for example on a colour test plate from a production run—and using the difference to calculate and simulate a correction formulation.

Moreover, using the method described, it is also possible to carry out a virtual simulation of a colour formulation for a particular paint or for a shade of the paint by selectively virtually combining the physical parameters of concentration and optical constants (K, S) of the pigments and hence their optical layer thickness, the concentration of the anisotropically light-scattering pigments and hence their surface density, angular distribution, pigment or particle size and thickness and the refractive indices, to take account of optical phase transitions.

This means that with the method described for simulating a colour formulation the optical properties of a number of known colour templates can be selectively virtually combined and in this way the optical properties of a known colour template can be replicated on the basis of physical parameters of pigments.

Furthermore, the present specification provides an apparatus for using the method described, with a substantially real or virtual uniform illumination with parallel radiation entry at a specific angle of incidence or illumination. Such uniform illumination can be achieved for example with an annular light source. Moreover, the apparatus comprises means for fixing an illumination geometry. For this purpose the apparatus comprises means for determining the angle of incidence of the illumination, which are described in more detail in Appendix 3. The major advantage of a perpendicular or annular illumination geometry is that the anisotropically light-scattering pigments incorporated in the paint layer or effect pigments with these illumination geometries on average have no azimuth dependency, with the result that the radiation transport equation can be treated in azimuth-independent manner.

Further embodiments of the proposed approach will become apparent from the specification and the attached drawings.

It should be understood that the features mentioned above and those to be explained hereinafter may be used not only in the particular combination specified but also in other combinations or on their own without departing from the scope of the present disclosure.

Some possible embodiments by way of example are schematically shown in the drawings and described in detail with reference to the drawings.

Figure 1:
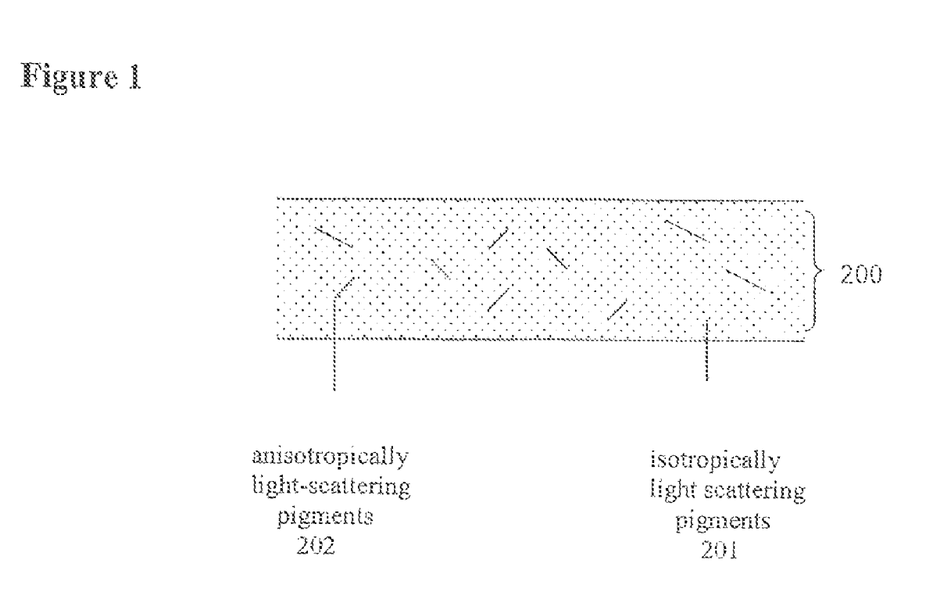
FIG. 1 shows a cross-section through a layer of a special effect paint with anisotropically and isotropically light-scattering pigments.

FIG. 1 shows a cross-section through a layer 200 of a special effect paint with anisotropically light-scattering pigments or special effect pigments 202 and isotropically light-scattering pigments 201 arranged within a layer of paint. The layer of paint thus comprises a combination of anisotropically light-scattering pigments 202 and isotropically light-scattering pigments 201. The anisotropically light-scattering pigments 202 are irregularly or randomly distributed within the paint layer and are significantly larger in size than the isotropically light-scattering pigments.

Figure 2:
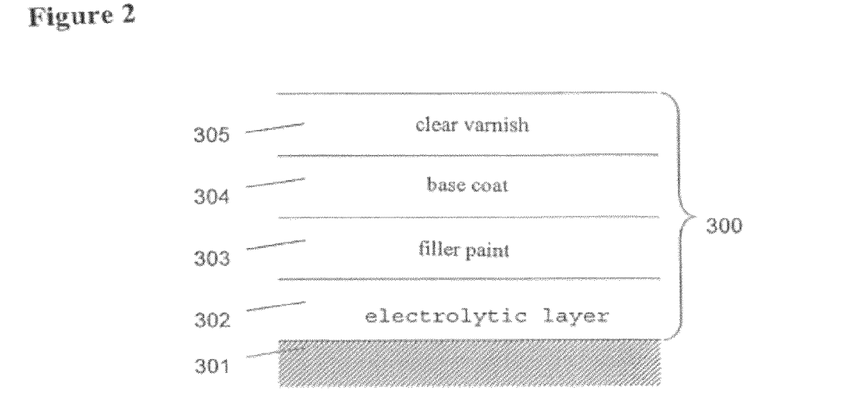
FIG. 2 shows a cross-section through a real multilayer paint structure.

FIG. 2 shows a cross-section through a real multilayered paint structure 300 on a substrate 301. This paint structure 300 consists of an electrolytically deposited primer layer 302, a coat of filler paint 303, a base coat 304 and a clear varnish 305 over the top. In this case, too, certain optical properties of the layers 302, 303, 304 and 305 may be taken into consideration in boundary conditions when solving linear differential equations. In this way it is possible to determine the influence of coloured substrates 302, 303 or the influence of the clear varnish 305 on the actual shade of colour of the base coat 304 or the multilayer paint structure 300.

Figure 3:
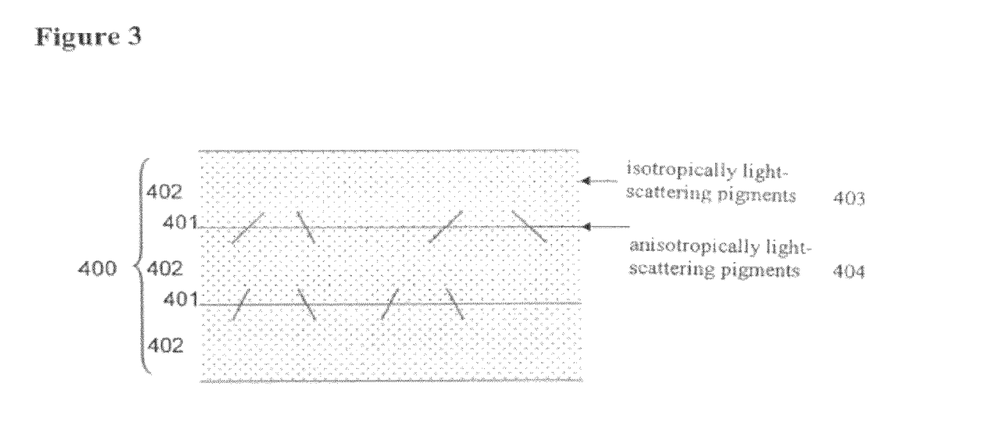
FIG. 3 shows a cross-section through a virtual multilayer paint structure with anisotropically light-scattering pigments arranged on inner edge surfaces.

FIG. 3 shows a virtual multilayered paint structure 400 which is divided into isotropically light-scattering layers 402 in which exclusively isotropically light-scattering pigments 403 are arranged. By contrast, anisotropically light-scattering pigments or special effect pigments 404 are virtually arranged on edge surfaces 401 of the isotropically light-scattering layers 402. The arrangement of the anisotropically light-scattering pigments 404 in this virtual multilayered paint structure 400, i.e. on the edge surfaces 401 of the layers 402 means that the anisotropically light-scattering pigments 404 do not have to be dealt with in differential equations but can be taken into consideration by means of boundary conditions, thus making it easier to solve the differential equations. The number of layers of the multilayered paint structure 400 can be chosen freely and adapted to the particular requirements.

FIG. 4a shows a schematic representation of an apparatus for applying annular illumination 501. An annular irradiation 505 is provided, which is aligned at an angle $\alpha$ 504 relative to a normal 503 of a paint surface 502. The angle $\alpha$ 504 thus constitutes an angle of incidence and can be adjusted for example by means of an apparatus 506, which is described in more detail in Appendix 3, according to a fundamental physical model. On the basis of a perpendicular or annular illumination geometry, the anisotropically light-scattering pigments incorporated in the paint surface 502 or in the layer of paint on average have no azimuthal dependency, which means that a radiation transport equation can also be dealt with in azimuth-independent manner.

FIG. 4b shows an apparatus analogous to FIG. 4a wherein the annular illumination is produced virtually by an annular superimposing of a real parallel individual illumination 501b with an angle of incidence $\alpha$ 504b relative to a normal 503b of a paint surface 502b. With an apparatus 506b, which is also described in more detail in Appendix 3, this angle $\alpha$ 504b can be adjusted according to the physical or mathematical model for the calculation.

Figure 5:
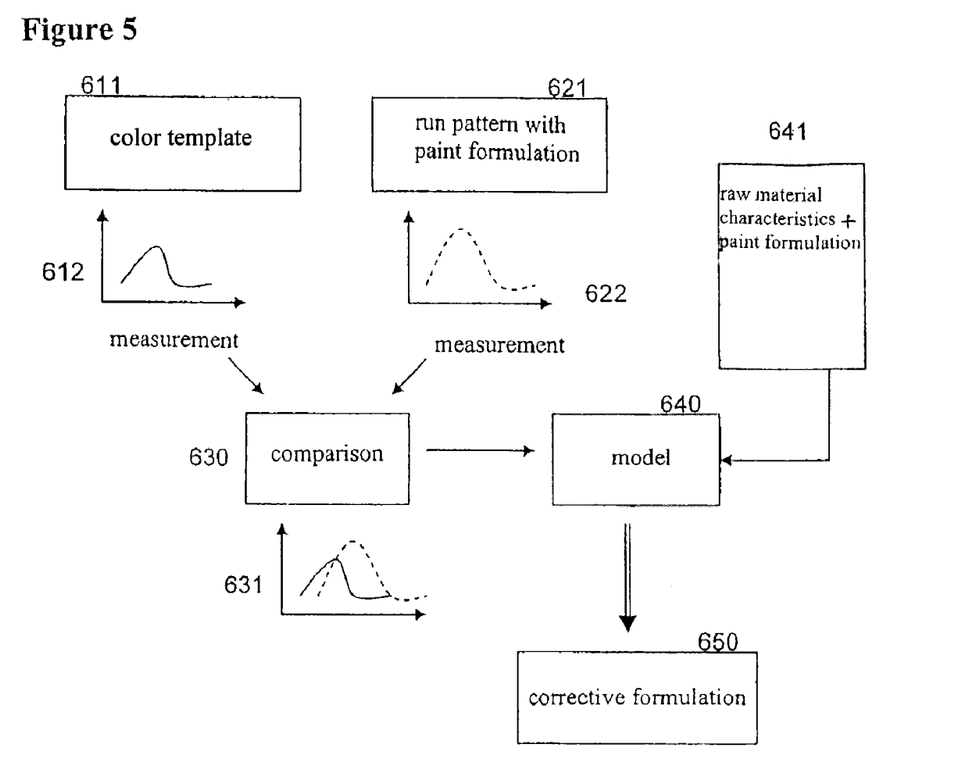
FIG. 5 shows a flow diagram of the process of reproducing a colour template.

FIG. 5 shows a flow diagram of a process for reproducing a colour shade of a colour template 611 of a special effect paint. Optical properties of the colour template 611 and a paint mock-up 621 (run pattern or colour test pattern) are determined and compared 630 in a measurement 612 or 622 using the method described, so that by means of a corrective calculation using a model 640 on which the method is based and inputting the raw material characteristics and paint formulation 641, a corrective formulation 650 of the paint mock-up 621 can be prepared by means of which it is possible to match the shade of colour of the template 611 with the shade of colour of the paint mock-up 621. For this purpose, in a first step, the optical properties of the colour template 611 are determined using the method described and laid down as a so-called desired value or in the form of a desired curve 612. Then the optical properties of a paint mock-up 621, which has been produced as a run sample using a provisional paint formulation, is also measured using the method described and the measured values 622 are compared with the desired value 612 of the colour template 611. If the two measurements 612, 622 differ from each other, a corrective formulation 650 based on the model 640 shown can be calculated and simulated using the method described. Using this corrective formulation 650, the shade of colour of the paint mock-up 621 can be adjusted to match that of the colour template 611.

Besides the reproduction of existing colour templates, the process described and the method described are also suitable for modelling and simulating new paint formulations.

Figure 6:
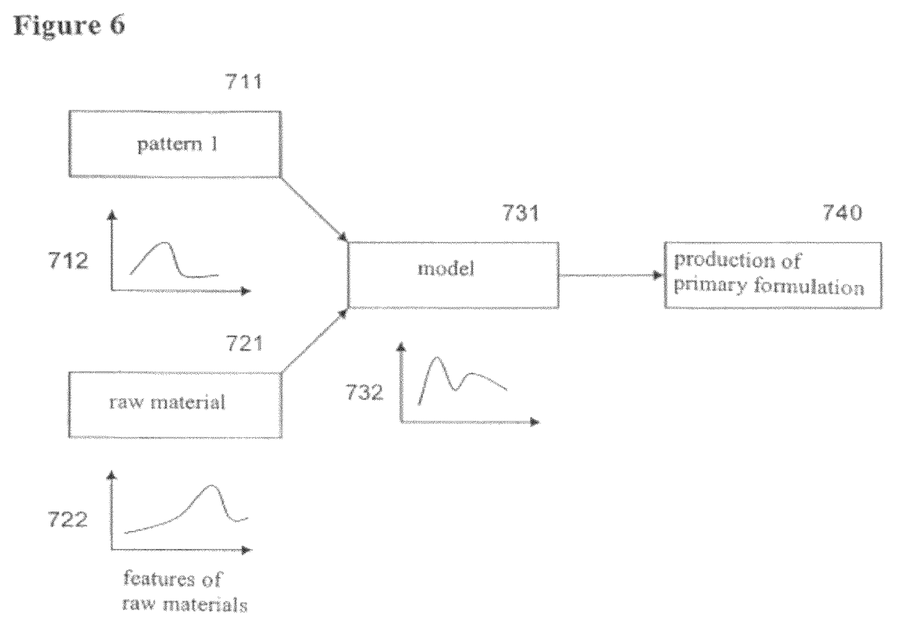
FIG. 6 shows a flow diagram of a process for creating a model and simulation of a new paint formulation.

FIG. 6 shows a flow diagram of a process for modelling and simulating a new paint formulation or primary formulation 740. For this, by measuring 712 a new colour pattern 711, a corresponding paint formulation is calculated using a model 731 as described and features 722 of its own raw materials 721. In this way, virtually a new paint formulation or primary formulation can be prepared according to the basic model 731, the composition 732 of which is thus precisely known. In particular this process or this method is suitable, as described, for modelling and simulating special effect paints and their formulations.

Figure 7:
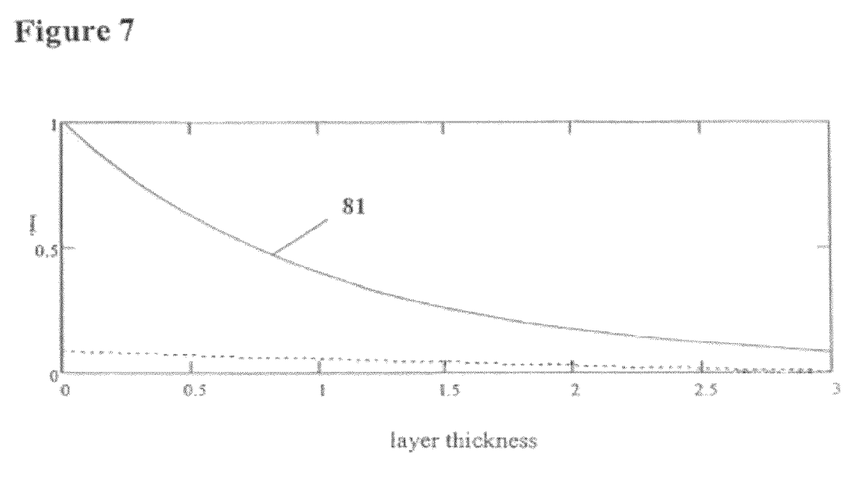
FIG. 7 shows the intensity of irradiation depending on the layer thickness of a paint according to a model for isotropically light-scattering pigments.

FIG. 7 shows an intensity of an irradiation or illumination dependent on a layer thickness of a paint according to a model for isotropically light-scattering pigments. A steadily decreasing trend 81 in the intensity as the layer thickness increases is clearly visible. The optical properties can be described approximately using this model by means of a linear differential equation system with constant coefficients which can be solved comparatively easily and with efficient use of computing time.

Figure 8:
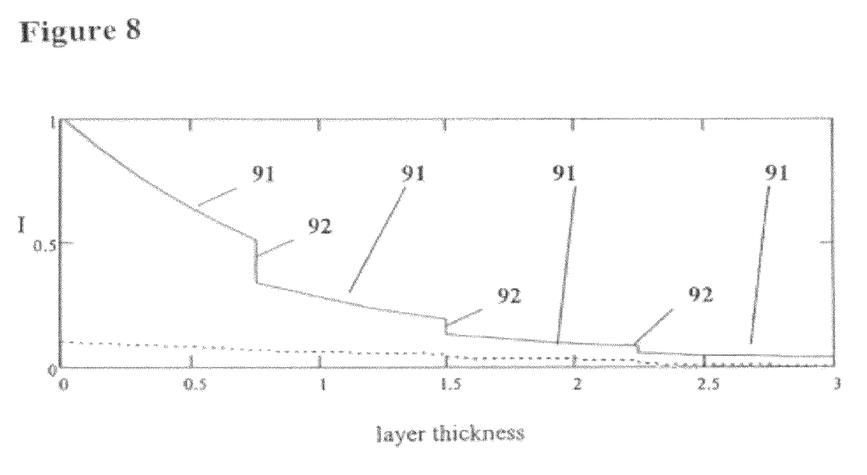
FIG. 8 shows the intensity of irradiation depending on the layer thickness of a special effect paint according to a model for anisotropically light-scattering pigments according to the disclosure.

FIG. 8 shows an intensity of an irradiation or illumination dependent on a layer thickness of a special effect paint by means of a model according to the disclosure for anisotropically light-scattering pigments. According to this, optical properties of the anisotropically light-scattering pigments on edge surfaces are taken into account. Characteristic is a steadily decreasing pattern of intensity only in certain areas. In these areas of a constant pattern 91, the optical properties of the isotropically light-scattering pigments are described by means of linear differential equations. At edge surfaces between the layers, effect-specific properties of the anisotropically light-scattering pigments, indicated by "steps" 92 in the intensity curve, are taken into consideration by means of suitably matched boundary conditions.

Figure 9:
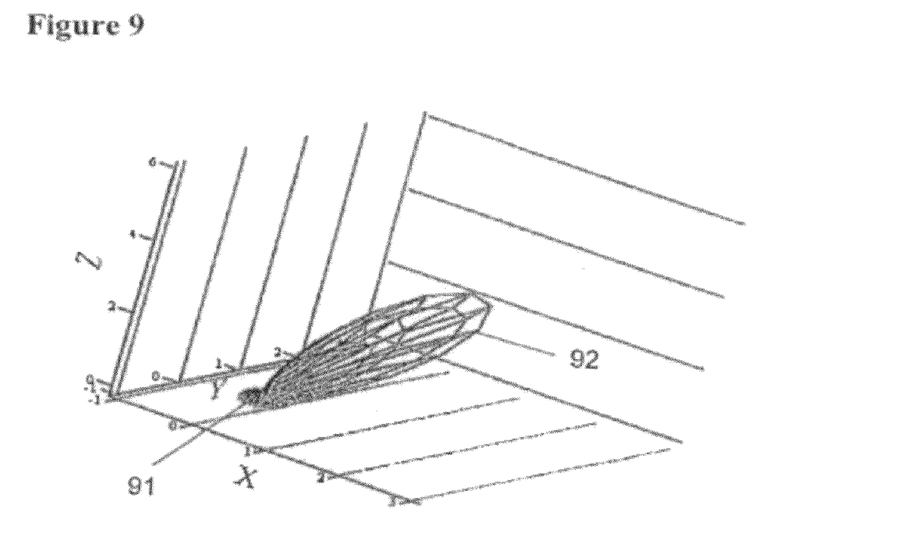
FIG. 9 shows a completed measuring indicator when a single illumination is used.

FIG. 9 shows a complete measuring indicator when using a single illumination at a specific angle of incidence, wherein the measuring indicator and its determination are described more fully in Appendix 3. The x-y plane shown constitutes a surface of the paint that delimits the paint from the surrounding area or the ambient air. The z coordinate shown faces in the direction of thickness of the paint or paint layer. Reference numeral 91 denotes a small area in the region of the x-y plane of the measuring indicatrix which is produced by the isotropically light-scattering pigments. The remaining part 92 of the measuring indicatrix extending spatially within the layer of paint, on the other hand, is caused by the anisotropically light-scattering pigments.

Figure 10:
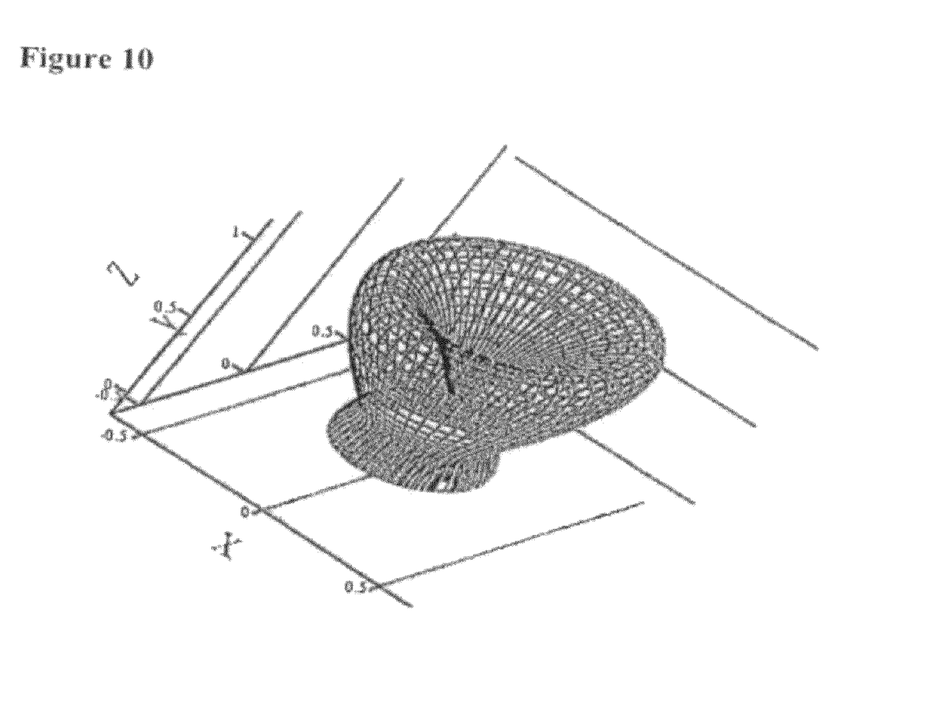
FIG. 10 shows a simulation of a measuring process where there is a virtual annular illumination.

FIG. 10 shows a simulation of a measuring process where there is virtual annular illumination by superimposing the completed measuring indicator from FIG. 9 for a number of n azimuth angles of the individual illumination source which thus provides the virtual annular illumination. A more detailed description of the simulation is provided in Appendix 3.

The virtual modelling, simulation and reproduction of shades of colour and the corresponding paint formulations provides a comparatively fast and simple way of testing new colour templates or shades of colour and combinations of colours, particularly of superimposed layers of paint, before real paints have to be mixed. In particular, this process can be used by means of the method described for special effect paints with anisotropically light-scattering pigments. The method thus provides a possible way of saving on raw materials and material costs as well as the labour costs which would otherwise be incurred in an experimental actual mixing of the colour shades.

APPENDIX 1

Detailed Explanation of the Radiation Transport Equation

A general form of a radiation transport equation (RTE) is an integro-differential equation which can be shown as follows:

$$\mu \frac{dI(\tau, \mu, \varphi)}{d\tau} = I(\tau, \mu, \varphi) - \frac{1}{4\pi} \int_{-1}^{+1} \int_{0}^{+2\pi} p(\tau; \mu, \varphi; \mu', \varphi') I(\tau, \mu', \varphi') d\mu' d\varphi' \quad (1.1)$$

In this equation
I is a desired radiation density,
p is a phase function,
$\tau$ is an optical thickness and
$\varphi$ is an azimuth angle.
$\mu$ is obtained from a height angle $\theta$ by the relation:

$$\mu = \cos(\theta) \quad (1.2)$$

In the case of rotational symmetry of the illumination and constancy of the phase function p, with $p=\omega$, the RTE is simplified to:

$$\mu \frac{dI(\tau, \mu,)}{d\tau} = I(\tau, \mu) - \frac{1}{2}\omega \int_{-1}^{+1} I(\tau, \mu') d\mu' \quad (1.3)$$

If the integral on the right-hand side of the RTE is solved (approximately) with a numerical quadrature formula with n support points in an interval [−1,1], e.g. according to Gauss-Radau, a linear differential equation system is obtained with constant coefficients $a_{i,j}$, i, j=1, . . . , n.

If the coefficients are arranged canonically in a matrix, this differential equation (DE) is written in the form:

$$\frac{dI}{d\tau} = I' = AI \quad (1.4)$$

The solution to this DE is (analogously to a one-dimensional case n=1):

$$I(\tau) = \exp(A\tau) * I(\tau=0) \quad (1.5)$$

The calculation of the (multidimensional) exponential function "exp( )" can be carried out by standard methods of linear algebra using eigenvalues or eigenvectors of the matrix A, so as to obtain a closed, approximate solution to the RTE.

APPENDIX 2

Detailed Description of the Effect Operator:

If the radiation transport equation (RTE) shown in Appendix 1 is solved for "normal" paints (i.e. the isotropically light-scattering pigments that give the colour are continuously distributed through the layer of paint) by approximating the integral of the RTE with a numerical quadrature formula and thus, as described in Appendix 1, the RTE is replaced by a linear differential equation system with constant coefficients, adequate boundary values that take account of the radiation intensity of the illumination must be given at the edge sides or on an outer surface of the paint.

In the case of special effect paints, boundary conditions or connection conditions must additionally be formulated on the basis of the model used on inner virtual interfaces or edge surfaces on which the effect-producing substances are arranged.

If an n-dimensional intensity vector I in the linear differential equation (1.5) shown in Appendix 1 above a boundary layer or edge surface is called I_S1 and below this is called I_S2, and if the first n/2 components of the n-dimensional intensity vector I associated with an upwardly directed beam or light beam of the illumination are given the index "up" and the remaining n/2 components are given the index "dn", the following intensity vectors are obtained, for example:

$$I\_S1 := \begin{pmatrix} I\_S1_{up} \\ I\_S1_{dn} \end{pmatrix} \quad I\_S2 := \begin{pmatrix} I\_S2_{up} \\ I\_S2_{dn} \end{pmatrix} \quad (2.1)$$

Then the following "inner" boundary or continuity conditions must be adhered to for the optical thickness τ on the inner interface or edge surface:

$$I\_S1_{up} = \eta SPR\, I\_S1_{dn} + (1-\eta) I\_S2_{up} + \eta * SPL * I\_S2_{up} \quad (2.2)$$

$$I\_S2_{dn} = \eta SPR\, I\_S2_{up} + (1-\eta) I\_S1_{dn} + \eta * SPL * I\_S1_{dn} \quad (2.3)$$

"SPR" and "SPL" here denote (n/2×n/2) matrices which are defined as follows, for example, for the case n=8:

$$SPL := \begin{pmatrix} p_2 & p_3 & p_4 & 0 \\ p_3 & p_4 & 0 & 0 \\ p_4 & 0 & 0 & 0 \\ 0 & 0 & 0 & 0 \end{pmatrix} \quad SPR := \begin{pmatrix} 0 & 0 & 0 & p_1 \\ 0 & 0 & p_1 & p_2 \\ 0 & p_1 & p_2 & p_3 \\ p_1 & p_2 & p_3 & p_4 \end{pmatrix} \quad (2.4)$$

The corresponding general case for n is obtained analogously in an obvious manner.

The matrices have general matrix coefficients $p_i$ which represent an angular distribution of the anisotropically light-scattering pigments or special effect pigments. The parameter η represents their surface density.

By canonical algebraic conversions the continuity conditions with an (n×n) matrix M can be represented in the compact matrix form

I_S2=M I_S1.

This matrix M is designated the effect operator.

APPENDIX 3

Description Relating to the Means for Determining an Angle of Incidence of an Illumination For using means for determining an angle of incidence of an illumination, first of all the appropriate angle of incidence α of the illumination must be determined. On this point it should be borne in mind that the incident light from the illumination onto an object for measurement where there is an optical phase transition, e.g. between the ambient air ($n_0$=1) and a paint or a cured paint binder ($n_1$=1.5), is deflected or distorted in its direction of propagation by an associated phase boundary as it passes through. At least one suitable angle of incidence α can be calculated initially using given refractive indices of the media present at the phase transition, by means of the so-called "Fresnel" relation and a corresponding quadrature formula.

In spectrophotometric measuring equipment that have means for determining the angle of incidence of the illumination, this calculated illumination angle can be set. However, the measuring instruments generally available do not have such means for determining the angle of incidence, but have a fixed angle of incidence of the illumination. The result of this is that a corresponding measuring instrument with a fixed angle of incidence has to be used which is as similar as possible to the angle of incidence calculated by means of the quadrature formula and "Fresnel" relation.

The means for determining the angle of incidence of the illumination are schematically shown as apparatus 506 and 506b in FIGS. 4a and 4b.

If the illumination is carried out according to the description of FIG. 4b using virtual illumination, the angle of incidence α is set analogously to the foregoing description.

Additionally, when a virtual annular illumination is used, the measurement is supplemented by extra steps. Virtual annular illumination denotes an individual light e.g. in the form of a point of light, which shines onto the object for measurement at a specific angle of incidence from a specific direction or at a specific azimuthal angle and is rotated along an annular track around the object for measurement while the angle of incidence remains constant but the azimuthal angle varies. Instead of using an annular illumination or light source, annular illumination can thus be replaced virtually by the single illumination.

First of all, the intensity of the light reflected from the object for measurement is measured outside the object for measurement at a constant angle of incidence and a constant azimuthal angle. By transformation of the measured values obtained from the measurement, the values of the intensity within the paint on the object for measurement and belonging to the measured values can be determined using the "Fresnel" relation. For example, only a few measured values are measured or only a few associated intensity values are determined.

Another step may comprise adapting or "fitting" a suitable so-called "fit" function to the intensity values and supplementing virtual intensity values which by suitable rotation of the "fit" curve about an angle of incidence form a so-called completed "inner" measuring indicatrix.

This means that first of all the intensity values present within the paint on the object for measurement which are approximated by the "fit" function are determined by transformation from the measurements measured outside the object for measurement. By rotation about the angle of incidence transformed into the interior of the paint a three-dimensional intensity distribution or the measuring indicatrix is calculated. The angle of incidence provides an angle of reflection comparable to a headlamp which is determined by a reflection of the incident light on the smooth surface of the paint. An example of a completed "inner" measuring indicatrix is shown in FIG. 9. The term "inner" means that this is an intensity distribution that occurs "inside" the paint but is not a part of the measurement carried out from outside.

The "fit" function may be represented as follows, for example:

$$a \cdot \exp\left(\frac{\theta^2}{2s^2}\right) + b$$

Here, θ represents an associated angle of aperture of the measuring indicatrix of the layer of paint.

Then a measuring process is simulated using a virtual annular illumination. This simulation is carried out by superimposing the completed measuring indicatrix which has been created for a specific azimuthal angle for a number n of different azimuthal angles. The superimposing of the measuring indicator for different azimuthal angles thus corresponds to a rotation of the illumination used along an annular track around the object for measurement, so as to simulate illumination from different azimuthal angles and thus simulate virtual annular illumination. FIG. 10 shows a representation of such a simulation or a measuring process with virtual annular illumination where n=36.

The invention claimed is:

1. A method of modeling and simulating optical properties in special effect paints which comprises:
   isotropic light-scattering pigments having isotropic light-scattering properties and optical properties, and
   anisotropic light-scattering pigments having anisotropic light-scattering properties and optical properties,
   wherein the special effect paints form at least one layer of material or coat of paint on a suitable substrate, and for reproducing a shade of color of a color template of a special effect paint,
   wherein the color template has optical properties and the optical properties of the color template and optical properties of a color test pattern of a formulation of a paint mock-up are determined and compared by a comparison process, so that using the comparison a correction can be made to the formulation for the paint mock-up and the shades of color of the color template and paint mock-up can be matched, and
   wherein the isotropic light-scattering pigments and the anisotropic light-scattering pigments are virtually spatially separated such that the isotropic light-scattering pigments virtually form the layer of material, wherein the layer of material has optical properties, and the anisotropic light-scattering pigments are virtually arranged on the edge surfaces of the layer of material, so that the optical properties of the virtual layer of material formed by the isotropic light-scattering pigments are determined by linear differential equations and the optical properties of the anisotropic light-scattering pigments are taken into consideration as boundary conditions, by means of specific effect operators.

2. The method according to claim 1, wherein the virtual layer of material of the isotropic light-scattering pigments comprises a virtual stacked multilayered structure having a number of virtual layers, wherein for each of these virtual layers, the anisotropic light-scattering pigments are arranged on the respective edge surfaces of the virtual layers.

3. The method according to claim 2, wherein the virtual stacked multilayered structure corresponds to a real multilayered structure of a special effect paint.

4. A method of reproducing a color template using the method according to claim 1, wherein the optical properties of the color template and the color test pattern of a formulation of a paint mock-up are measured and compared, and from a difference a corrective formulation is calculated and simulated.

5. A method of simulating a paint formulation using the method according to claim 1, wherein optical properties of a known color template are simulated on the basis of physical parameters of raw materials of paints.

6. An apparatus for modeling and simulating one or more optical properties of a special effect paint, comprising:
   a real or virtually uniform illumination source with parallel radiation entry,
   an illumination angle fixer that fixes an illumination geometry, and
   an instrument that determines an angle of incidence of the illumination,
   wherein the apparatus models and simulates optical properties of a special effect paint comprising at least one isotropic light-scattering pigment and at least one anisotropic light-scattering pigment by comparing optical properties of a color template of the special effect paint with a color test pattern by virtually arranging the anisotropic light-scattering pigments on an edge surface of a virtual layer of the light-scattering pigment in a layer of the special effect paint such that optical properties of the virtual layer are determined by linear differential equation and optical properties of the anisotropic light-scattering pigment are taken into consideration as one or more boundary conditions according to one or more specific effect operators.

7. A method for at least one of modeling and simulating one or more optical properties of a special effect paint, wherein the special effect paint comprises at least one isotropic light-scattering pigment and at least one anisotropic light-scattering pigment, and wherein the special effect paint is in the form of a layer on a substrate, comprising:
   determining optical properties of a color template;
   determining optical properties of a color test pattern;
   comparing the optical properties of the color template and the optical properties of the color test pattern to identify one or more differences between the optical properties of the color template and the optical properties of the color test pattern,
   wherein the determining is carried out by virtually spatially separating the isotropic light-scattering pigment and the anisotropic light-scattering pigment to form a virtual layer comprising the isotropic light-scattering pigment, wherein the virtual layer has edge surfaces on which the anisotropic light-scattering pigment is virtually arranged,
   wherein the determining further includes linear differential equation analysis of optical properties of the virtual layer wherein the optical properties of the anisotropic light-scattering pigments are taken into consideration as boundary conditions to the virtual layer according to one or more specific effect operators.

8. The method according to claim 7, wherein the virtual layer comprising the isotropic light-scattering pigment has a virtual stacked multilayer structure and, for each stacked layer, the anisotropic light-scattering pigment is virtually arranged on the edge surface of the virtual stacked layers.

9. The method according to claim 8, wherein the virtual stacked multilayer structure represents a multi-layered structure of a special effect paint.

10. The method according to claim 7, further comprising:
    determining a corrective formulation for the special effect paint according to a difference between the optical properties of the color template and the optical properties of the color test pattern.

11. The method according to claim 7, further comprising:
    simulating optical properties of a known color template according to physical parameters of one or more paint raw materials.

12. A method for producing a special effect paint comprising at least one isotropic light-scattering pigment and at least one anisotropic light-scattering pigment, comprising:

determining optical properties of a color template of the special effect paint, determining optical properties of a color test pattern of a paint formulation, comparing the optical properties of the color template and the paint formulation to identify one or more differences between the optical properties of the color template and the optical properties of the paint formulation, wherein the optical properties of the color template and the paint formulation are determined by virtually spatially separating the isotropic light-scattering pigments and the anisotropic light-scattering pigments to form a virtual material layer comprising the isotropic light-scattering pigments, wherein the virtual material layer has edge surfaces on which the anisotropic light-scattering pigment is virtually arranged, and wherein the optical properties are determined by linear differential equation analysis correcting for the anisotropic light-scattering pigment virtually arranged on the edge surface of the virtual material layer according to one or more specific effect operators, and changing the paint formulation according to the differences obtained by the comparing of the optical properties of the color template and the optical properties of the paint formulation.

* * * * *